United States Patent
Erkoboni et al.

(10) Patent No.: US 6,596,312 B1
(45) Date of Patent: Jul. 22, 2003

(54) HYDROLYZED CELLULOSE GRANULATIONS OF SALTS OF DRUGS

(75) Inventors: David F. Erkoboni, Pennington, NJ (US); Ronald S. Vladyka, Jr., Somerset, NJ (US); Christopher A. Sweriduk, Chalfont, PA (US); Andrew J. Favara, New Egypt, NJ (US)

(73) Assignee: R.P. Scherer Technologies, Inc., Paradise Valley, NV (US)

( * ) Notice: Subject to any disclaimer, the term of this patent is extended or adjusted under 35 U.S.C. 154(b) by 0 days.

(21) Appl. No.: 09/669,533

(22) Filed: Sep. 26, 2000

Related U.S. Application Data

(60) Provisional application No. 60/156,547, filed on Sep. 29, 1999.

(51) Int. Cl.$^7$ .............................. A61K 9/20; A61K 9/14
(52) U.S. Cl. ........................ 424/464; 424/465; 424/489
(58) Field of Search ............................... 424/464, 465, 424/489, 451

(56) References Cited

U.S. PATENT DOCUMENTS

| | | | |
|---|---|---|---|
| 2,978,446 A | 4/1961 | Battista et al. | 260/212 |
| 3,111,513 A | 11/1963 | Battista et al. | 260/212 |
| 4,859,704 A | * 8/1989 | Haas | 514/557 |
| 5,585,115 A | 12/1996 | Sherwood et al. | 424/489 |
| 5,712,310 A | 1/1998 | Koch | 514/570 |
| 5,725,886 A | 3/1998 | Erkoboni et al. | 424/499 |
| 5,858,409 A | * 1/1999 | Karetny et al. | 424/489 |
| 6,197,336 B1 | * 3/2001 | Grassano et al. | 424/464 |

* cited by examiner

Primary Examiner—Thurman K. Page
Assistant Examiner—Rachel M. Bennett
(74) Attorney, Agent, or Firm—Donald O. Nickey

(57) ABSTRACT

The present invention provides a method for preparing a spray-dried, compressible granular formulation for preparing pharmaceutical tablets in which essentially water-insoluble, acidic, amphoteric, and basic pharmaceutically active agents are converted to more water-soluble salts which are granulated with hydrolyzed cellulose, drug-containing slurries, the resulting granulations, capsules containing granulations, and pharmaceutical tablets compressed from such granules. In these formulations there is employed from 1% to 85% by weight of the pharmaceutically active agent and its salt form, from 5% to 99% of hydrolyzed cellulose, based on the dry weight of the granulation, and optionally, conventional granulation and/or tableting additives such as surfactants, disintegrants, and antiadherents/flow aids. Said tablets have significantly increased dissolution of the pharmaceutically active agent at the pH of the gastrointestinal tract in comparison with the unconverted free pharmaceutically active agent.

1 Claim, 3 Drawing Sheets pH - Solubility Profile pH - Solubility Profile

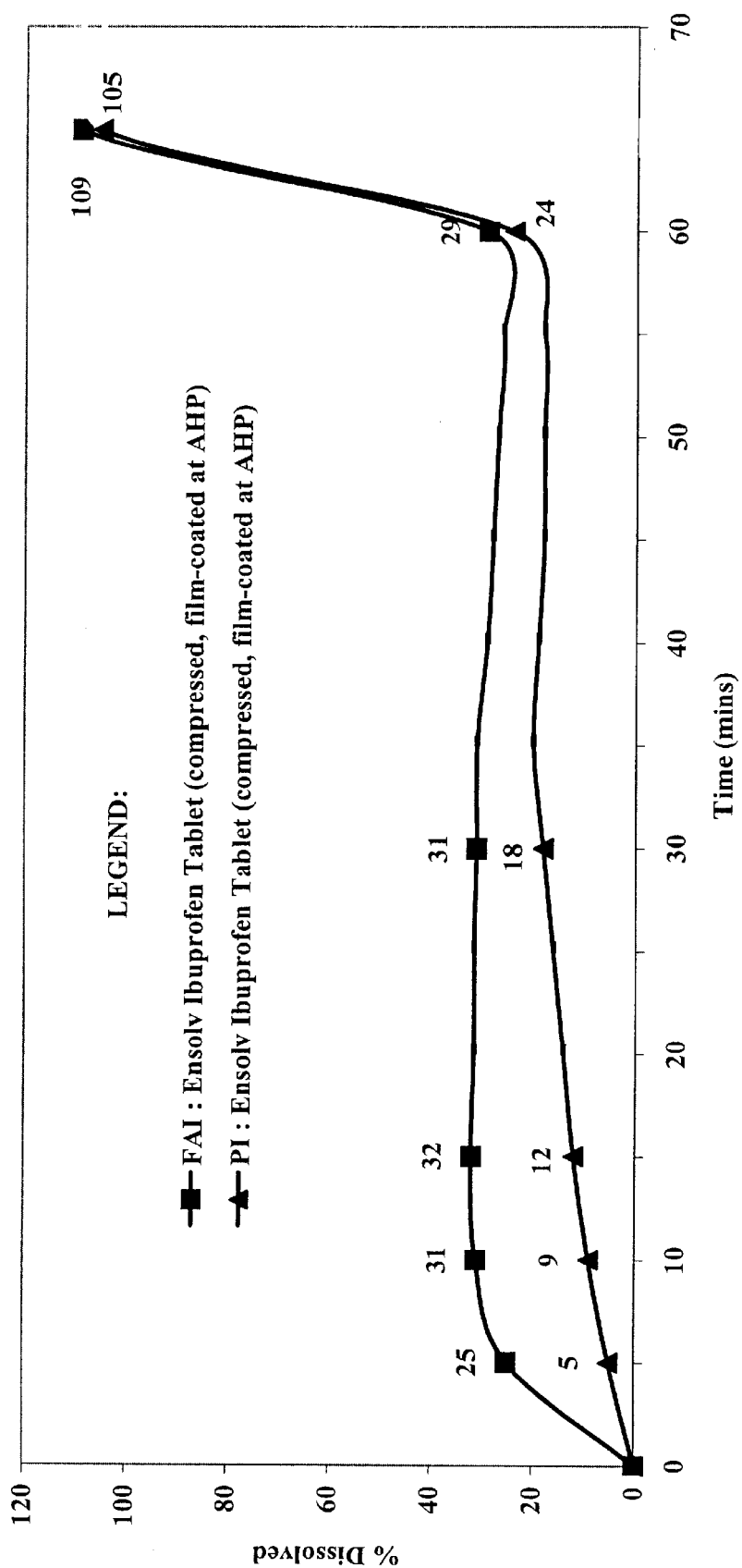

HYDROLYZED CELLULOSE GRANULATIONS OF SALTS OF DRUGS

PRIOR APPLICATION DATA

The present application claims the benefit of U.S. Serial No. 60/156,547, filed Sep. 29, 1999.

FIELD OF THE INVENTION

The present invention relates to a method for granulation of relatively water-insoluble pharmaceutically active agents capable of forming a salt, to granular formulations thereof, and to pharmaceutical tablets made from such granular formulations. More specifically, the invention relates to drying an aqueous slurry of hydrolyzed cellulose or microcrystalline cellulose and one or more relatively water-insoluble pharmaceutically active agents which have at least partially been converted to more water-soluble salts to form granular formulations for use in the manufacture of pharmaceutical tablets and in filling capsules. The methods and compositions of this invention are particularly useful for relatively water-insoluble pharmaceutically active agents, such as salts of ibuprofen, which are not readily compressible into tablets after being dry blended with excipients. Compressible compositions containing salts of these relatively water-insoluble pharmaceutically active agents have greatly increased rates of dissolution.

BACKGROUND OF THE INVENTION

Certain pharmaceutically active agents present challenges to dosage formulation. Ibuprofen, for example, is difficult to compress into tablets from a dry mix of excipients as heretofore practiced in the art. This lack of compressibility was overcome by a spray drying granulation technique described in U.S. Pat. No. 5,858,409. In the process described in this patent, hydrolyzed cellulose and the pharmaceutically active agent are mixed in a slurry, optionally with other excipients. This slurry is then spray dried to produce a granular composition which advantageously is comprised of granules, 90% of which are larger than 50 microns and smaller than about 500 microns. The median granule size is typically in the range of about 150 to 300 microns. Granules that are produced by this method are relatively porous, free flowing, substantially spherical, and readily compressible into pharmaceutical tablets having improved hardness, decreased friability, and excellent dissolution characteristics.

SUMMARY OF THE INVENTION

The present invention provides methods for granulating pharmaceutically active agents that have been at least partially converted into salts that are more water-soluble. These methods comprise mixing hydrolyzed cellulose, an aqueous solvent, and a relatively water-insoluble pharmaceutically active agent that has been at least partially converted into a more water-soluble salt form. In certain preferred embodiments, the methods of the invention comprise the steps of preparing a slurry that includes hydrolyzed cellulose, an aqueous solution of the salt form of a pharmaceutically active agent, and optionally, other excipients, and then drying the slurry.

The present invention also provides compositions comprising hydrolyzed cellulose in immixture with an aqueous solution that includes at least one relatively water-insoluble pharmaceutically active agent that has been at least partially converted into its more water-soluble salt form. Such compositions preferably are prepared either by adding a solution containing the salt form of the pharmaceutically active agent to a slurry of hydrolyzed cellulose in an aqueous solvent, or by adding the pharmaceutically active agent to the slurry and then at least partially converting it to its salt form in situ by reacting it with a suitable acid and/or base. Accordingly, one aspect of the present invention relates to compositions comprising hydrolyzed cellulose, water, at least one relatively water-insoluble pharmaceutically active agent, and an acid or base that is capable of reacting with said relatively water-insoluble pharmaceutically active agent and thereby converting it at least partially into its more water-soluble salt form.

In another aspect, the invention provides granular compositions that are produced by the drying process. These compositions contain about 1 percent to about 95 percent by weight of the relatively water-insoluble pharmaceutically active agent which has been at least partially converted into its more water-soluble salt and about 5 percent to about 99 percent by weight of hydrolyzed cellulose. In yet another aspect, the invention provides pharmaceutical tablets manufactured by compression of the granular composition of this invention which provide unexpectedly superior dissolution of the pharmaceutically active agent.

Dissolution of relatively insoluble pharmaceutically active agents which can be converted to a salt is significantly improved by conversion of at least a portion of the pharmaceutically active agent to its more water-soluble salt form in accordance with the present invention.

BRIEF DESCRIPTION OF THE FIGURES

FIG. 3 shows dissolution profiles of free acid ibuprofen spray dried with hydrolyzed cellulose and formed into tablets (FAI), and ibuprofen which had been at least partially converted into potassium salt, spray dried with hydrolyzed cellulose and formed into tablets (PI) at low pH for 60 minutes before adjusting pH to >6.0.

DETAILED DESCRIPTION OF THE INVENTION

Figure 1:
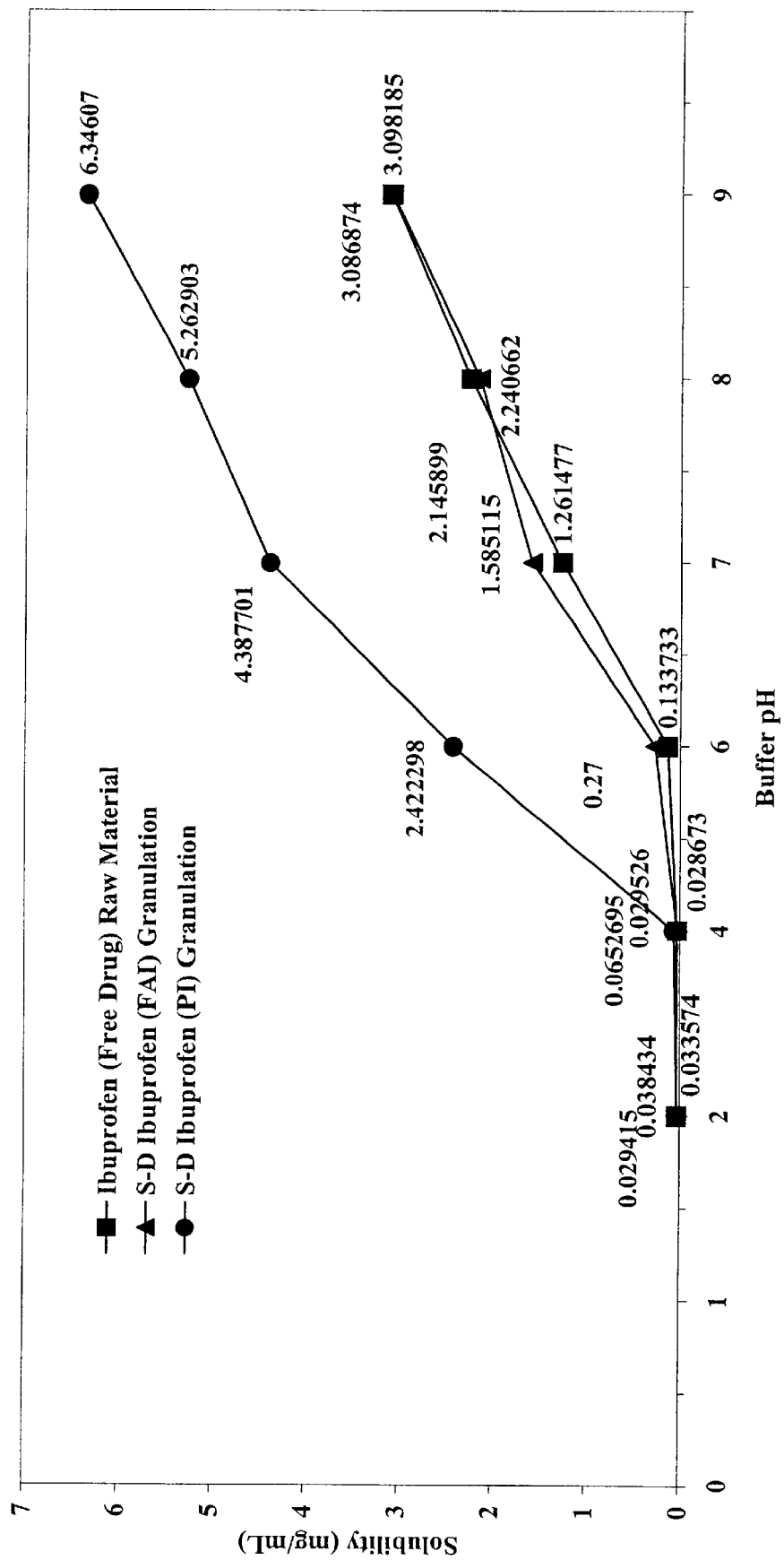
FIG. 1 shows a comparison of the solubility of unprocessed ibuprofen, free acid ibuprofen which has been spray dried with hydrolyzed cellulose (FAI), and ibuprofen which has been at least partially converted into potassium salt and has been spray dried with hydrolyzed cellulose (PI).

It has been discovered that certain difficulties typically encountered in preparing solid dosage forms containing relatively water-insoluble pharmaceutically active agents can be overcome by placing the free acid or free base of the pharmaceutically active agent in solution, together with a compound that provides a counter-ion (e.g., an acid or base), so as to form a solution containing a salt of the pharmaceutically active agent. Alternatively, the free acid or free base of the pharmaceutically active agent may be mixed with all of the ingredients of the dosage form, including the compound that provides the counter-ion, at once, thus allowing the conversion of the relatively water-insoluble pharmaceutically active agent to its more water-soluble salt in situ. The salt-containing solutions of the invention optionally can be mixed with other ingredients of the dosage form before they are dried down to produce generally porous and spherical granules suitable for compression into tablets.

As used herein, the term "relatively water-insoluble" refers to compounds and compositions that are either insoluble or practically insoluble (greater than or equal to 10,000 parts of solvent required for 1 part of solute), very slightly soluble (from 1,000 to 10,000 parts of solvent required for 1 part of solute), slightly soluble (from 100 to 1,000 parts of solvent required for 1 part of solute), or sparingly soluble (from 30 to 100 parts of solvent required for 1 part of solute) in water, as defined in the U.S. Pharmacopeia, Remington: Pharmaceutical Science, 18$^{th}$ Edition, Mack Publishing Co., and as used in the industry by those of ordinary skill in the art, irrespective of dose.

As used herein "converted" refers to partial or complete conversion. That is, when referring to a relatively water-insoluble pharmaceutically active agent that has been converted to its more water-soluble salt, it is meant that at least some amount of the relatively water-insoluble pharmaceutically active agent has been converted to its more water-soluble salt.

As an example, and not by way of limitation, ibuprofen, in its free acid form, is relatively water-insoluble and has a melting point of about 70° C. When converted to its potassium salt, however, the melting point of ibuprofen decreases to about 50–55° C. This decrease in melting point presents a formulation problem in that the frictional forces generated during tableting of ibuprofen typically are higher than the melting point of the ibuprofen salt. Thus, if one tableted formulations containing ibuprofen salts in a conventional method, this would tend to result in adherence of the formulation to the tableting equipment and produce inferior tablets. Furthermore, as the ibuprofen salt is more hygroscopic than the free acid, it is not practical to dry the salt to make tablets by conventional means.

In the process aspect of this invention, an aqueous slurry of hydrolyzed cellulose may be employed, which is in large measure responsible for the improved properties of the granular formulations of US Pat. No. 5,858,409 and for the improved tablets made therefrom. The compositions of this invention have dissolution characteristics that are directly traceable to the use of the salt of the relatively water-insoluble pharmaceutically active agents in combination with hydrolyzed cellulose. In this aspect, the invention thus provides a process for preparing a granular composition for filling capsules or preparation of tableted pharmaceutical dosage forms comprising the steps of (a) intimately mixing the pharmaceutically active agent, either converted partially or completely to its salt, with a smooth, uniform aqueous slurry of hydrolyzed cellulose to form a smooth, uniform aqueous slurry comprising hydrolyzed cellulose and the pharmaceutically active agent; and (b) drying the resulting slurry at a temperature below the charring temperature of the hydrolyzed cellulose. The advantages and benefits of this invention are most readily achieved when spray drying is selected as the method of drying, and the conditions for spray drying are selected to produce spray-dried particles which are relatively porous and substantially spherical, in which about 90% of the particles are larger than about 50 microns and smaller than about 1000 microns, and the median particle size is between about 150 microns and about 500 microns. It is a further advantage of the present invention to include in the slurry additional granulation and tableting additives (i.e., excipients) such as binders, fillers, disintegrants, flow aids, antiadherents, and/or surfactants, so that the resulting granules may be directly compressed into tablets with the addition of nothing more than a lubricant.

As used in this specification and claims, the term "hydrolyzed cellulose" means a cellulosic material prepared by acid hydrolysis of cellulose, and includes hydrolyzed cellulose that has been dried (e.g. microcrystalline cellulose) as well as hydrolyzed cellulose that has been maintained in an at least partially hydrated form. Thus, in some embodiments, the composition may comprise hydrolyzed cellulose that was previously dried to form microcrystalline cellulose, or, in other embodiments, the composition may comprise hydrolyzed cellulose that has been maintained in a hydrated state. In preferred embodiments, the hydrolyzed cellulose includes water of hydration from about 30–90%, typically from about 50–80%, and more preferably from about 55–65%. Although there are different ways of effecting hydrolysis of cellulose, a typical method for preparing hydrolyzed cellulose comprises the treatment of original cellulosic material, for example, wood-derived pulp, with an inorganic acid such as 2.5N hydrochloric acid solution for 15 minutes at the boiling temperature. This treatment has the effect of reducing the degree of polymerization (DP) to a relatively constant level. A DP of 125 means that the chain of cellulose is composed of 125 anhydroglucose units. Higher DP values represent longer chain lengths of cellulose, and lower values represent shorter chain lengths. The hydrolyzed cellulose in the slurries utilized wherein should have a minimum of 85% of the material with a DP of not less than 50 nor more than 550. More preferably, 90% of this material should have a DP within the range of 75 to 500. Even more preferably, 95% of the material should have a DP of 75 to 450. The level-off average DP, that is, the average of the total hydrolyzed cellulose sample which is consistently approached for a particular type of pulp, should be in the range of 200 to 300. The source of the pulp being hydrolyzed results in variations of the level-off DP. Hydrolyzed cellulose as used in this invention is a known composition more fully described as level-off DP in U.S. Pat. Nos. 2,978,446 and 3,111,513.

The hydrolysis step described above effectively destroys non-cellulosic components of the starting material as well as the fibrous, amorphous structure of the cellulose, leaving the crystallite material that is described above. Heretofore, the usual practice has been to dry this material after it has been washed with water to remove the acid and all soluble residues from the hydrolysis. A common method of drying is spray drying. Spray drying is the method in general use for the preparation of microcrystalline cellulose which may also be used beneficially with pharmaceutically active agents which have at least partially been converted to a salt. It has been found that spray drying the crystallites prior to granulation with pharmaceutically active agents can make the cellulose particles more dense and less compressible.

The use of hydrolyzed cellulose that has not been previously dried results in improved compressibility of the granular composition when it is dried. Drying slurries of hydrolyzed cellulose and pharmaceutically active agents that have partially or completely been converted to their more water-soluble salts (and, optionally, other excipients) provides advantageous formulations.

The process to prepare the granulations of this invention typically begins with a slurry of hydrolyzed cellulose in water. The term "slurry," as used herein, is intended to mean an aqueous suspension of hydrolyzed cellulose particles which have not been previously dried through application of heat or other evaporative means, as well as an aqueous suspension of microcrystalline cellulose reconstituted in an aqueous solvent. It is, however, intended to include a slurry of hydrolyzed cellulose from which a significant amount of water has been removed by mechanical means such as filtration. The water content may be reduced from about 90% to 55–65% to produce a suitable, dewatered starting material for use in the present invention. Reconstitution for use in this process is accomplished by the simple addition of water to the material, followed by thorough mixing. Preferably, the reconstituted slurry used as the starting material in the process will contain about 15% to about 25% by weight solids. In certain embodiments, it is preferred to use a form of hydrolyzed cellulose that has been maintained in at least a partially hydrated form.

As used in this specification, the phrase "at least partially converted to a more water-soluble salt" means that the conversion to a salt has proceeded to a point that at least some amount of the relatively water-insoluble pharmaceutically active agent is in its more water-soluble salt form. As a practical matter, at least about 5% of the pharmaceutically active agent should be converted to the salt, and usually greater than about 20% is converted to the salt to cause this change in solubility. There will, of course, be situations when the conversion will have to be 100% to be completely effective.

The pharmaceutically active agent can be added to this hydrolyzed cellulose slurry, and the resulting slurry mixed thoroughly. Depending upon the pharmaceutically active agent, the pharmaceutically active agent may be partially or completely converted to its more water-soluble salt prior to addition to the slurry; alternatively, the conversion can take place in the slurry after the addition of the pharmaceutically active agent has been completed. The choice of the method of operation may be influenced by the handling characteristics of both the pharmaceutically active agent and its salt form. For example, and not by way of limitation, ibuprofen does not require complete conversion to its potassium salt for complete dissolution of the ibuprofen in an aqueous environment. Rather, the presence of about 10% up to about 75% of the salt in an aqueous environment is sufficient to cause complete dissolution of the acidic ibuprofen. Thus, it may be preferable to prepare a solution of ibuprofen and its potassium salt (about 3:1 to about 1:1) in water before adding it to the slurry. This is not to say that ibuprofen cannot be added to the slurry prior to salt formation. In certain embodiments, when the pharmaceutically active agent is combined in solution with the compound that provides the counter ion (e.g., an acid or base) before either is added to the slurry of hydrolyzed cellulose, the resulting salt preferably does not precipitate out of solution. The salt solution can then be added to the aqueous slurry of hydrolyzed cellulose and any other excipients desired. The resulting slurry is then dried. Alternatively, the pharmaceutically active agent may be added to the aqueous slurry of hydrolyzed cellulose simultaneously with the compound that provides the counter ion, or before the compound that provides the counter ion and any other excipients desired. For some pharmaceutically active agents, it is preferred that the pharmaceutically active agent is converted into its salt form in situ, i.e., with the salt conversion taking place in the presence of the aqueous slurry of hydrolyzed cellulose.

The ratio of pharmaceutically active agent to cellulosic solids in the slurry is directly proportional to the ratio of these components in the finished granular formulation and ultimately in the tableted pharmaceutical product. As indicated below this may extend over a wide range in that the finished granule may contain from about 1 to 95% of the pharmaceutically active agent and from about 5 to 99% of cellulosic solids, the balance, if any, being conventional granulation and tableting aids, such as binders, fillers, disintegrants, flow aid, antiadherents, surfactants, lubricants, and/or any other excipients used in the art.

Sufficient water is added, if necessary, to provide a slurry having the maximum amount of solids that will permit the slurry to be pumped to a dryer. Maximizing the solids content minimizes the energy required for granulation and also has a beneficial effect on particle size and size distribution of the resulting granules. It is also advantageous to homogenize the slurry to provide a smooth, homogeneous suspension prior to drying.

The solids content of the drug-containing slurry is advantageously between about 10 and about 70 weight percent of the slurry, preferably about 20 to about 60 weight percent, even more preferably about 30 to about 60 weight percent. It is well recognized that the viscosity of a slurry is dependent on the percentage of the solids in the slurry, and the use of the more water-soluble salts does not contribute significantly to the slurry viscosity. Consequently, the use of more water-soluble salts of relatively water-insoluble pharmaceutically active agents enables one to employ a higher solids content than would be possible if the unconverted, relatively water-insoluble pharmaceutically active agent were to be used in the slurry when it is dried. This increase in the solids content represents a significant improvement over processes in which lower solids content must necessarily be used with a concomitant increase in water to be removed in the drying step.

The drug-containing slurry of the invention is dried such that slurries of various concentrations are obtained. Depending on the method of drying employed and the rate of dehydration, such composition contain greater than about 10–60% solids, more preferably the slurry is dried to contain greater than about 60–95% solids, more preferably, the slurry is dried to contain greater than about 97.5% solids.

As will be understood by those skilled in the art, the specific type of dryer employed is not critical to the success of this invention. Drying may be done in a spray dryer, for example, a disk dryer or a tower dryer, a fluid bed dryer, by vacuum drying, freeze drying, or by flash drying. Spray drying is the preferred method of drying. If a disk spray dryer is utilized, a large diameter dryer, such as the one in Example 1, is preferred to avoid producing smaller, denser granules, which are useful, but are not preferred. In spray drying, it will also be appreciated that the method of atomization is important to the production of granules having the correct size and characteristics. In these regards some experimentation may be required to optimize the process for a particular blend of hydrolyzed cellulose and the more water-soluble salt of a relatively water-insoluble pharmaceutically active agent.

In spray drying, an important aspect of the process is the control of temperature within the spray dryer. The outlet temperature must be carefully controlled to avoid charring the hydrolyzed cellulose. The use of the salt of a pharmaceutically active agent, however, may obviate a requirement that the temperature also be below the melting point of the pharmaceutically active agent unless the conversion to the salt is partial, thus leaving a significant amount of unconverted pharmaceutically active agent as in Example 1 below. An outlet temperature above about 120° C. will char the cellulose, making it a requirement that the outlet temperature not exceed this temperature. Lower temperatures, even those below the melting temperature of the unmodified pharmaceutically active agent may still be preferred, and may be selected for each pharmaceutically active agent as appropriate. Temperatures within the range of about 40° C. to about 115° C. are advantageous, and preferred temperatures are in the range of about 40° C. to about 105° C.

The spray-dried granular product of this invention will normally contain less than 10% by weight moisture. To obtain granular materials having the preferred 5% moisture content or the most preferred moisture content of 2.5% or less, it may be advantageous to place a fluid bed dryer in series with the spray dryer. This final step does not alter the granule size, but merely removes additional water from the granules.

In accordance with the second aspect of this invention, the resulting granular composition comprises (a) from about 1 percent to about 95 percent by weight of a salt of the pharmaceutically active agent or a mixture of the pharmaceutically active agent and its salt and (b) from about 5 percent to about 99 percent by weight of hydrolyzed cellulose. The optimum ratio of pharmaceutically active agent to hydrolyzed cellulose may be obtained through routine experimentation. Even though the conversion of the relatively water-insoluble pharmaceutically active agents into salts contained in the granular formulation of the invention can significantly improve the handling characteristics of the pharmaceutically active agents, there are residual effects that, when the granulations are compressed into tablets, can, for example, cause sticking to the tooling, thereby producing defective tablets. As a rule, these problems can be readily and routinely counteracted by altering the amount of hydrolyzed cellulose in the granulation, such as, for example, by increasing the amount of hydrolyzed cellulose.

In exceptional cases this may be insufficient to overcome these problems. Although the granulation may already contain optional ingredients, including disintegrants, flow aids, surfactants, lubricants, fillers, binders, and/or antiadherents, etc., it will be possible to overcome the problem by mixing microcrystalline cellulose, lubricant, and additional disintegrant, flow aid, and filler with the granules before tableting is performed.

A preferred formulation for granules containing a mixture of ibuprofen and its potassium salt (in a ratio of about 3:1 to about 1:1) would contain from about 30% to about 80% by weight of the pharmaceutically active agent and its salt, from about 20% to about 70% of hydrolyzed cellulose, from about 1% to about 10% of a disintegrant, preferably croscarmellose sodium, from about 0.5% to about 5% flow aid, e.g., colloidal silicon dioxide, and 0.05% to about 0.40% surfactant, preferably sodium lauryl sulfate. All percentages are by weight of the finished (i.e., dry) granules.

This process is applicable to all pharmaceutically active agents, preferably those which, in their unmodified state, are relatively water-insoluble, as that term is used herein with reference to the U.S. Pharmacopeia and known to those of skill in the art. This includes acidic, amphoteric, and basic pharmaceutically active agents. In many cases, pharmaceutically active agents belonging to these categories may be easier to handle in their unconverted state and then converted to the appropriate salt during the granulation process, either in aqueous solution apart from the hydrolyzed cellulose slurry, or in situ (i.e, in the presence of the hydrolyzed cellulose). Conversely, in some situations it may be preferable to handle the salt rather than the unconverted pharmaceutically active agent. As a consequence, this is a very versatile process which, in addition to the significantly improved dissolution characteristics provided by the salts of pharmaceutically active agents, provides an improved method of processing difficult-to-handle pharmaceutically active agents.

For conversion to a more water-soluble salt, an acidic pharmaceutically active agent has, for example, a labile hydrogen atom, which can be neutralized with a base. Appropriate bases include, but are not limited to, sodium, potassium, ammonium, quaternary ammonium, magnesium, and calcium hydroxides. The cations appropriate for the salts of pharmaceutically active agents are limited to those that produce more water-soluble salts and do not contribute physiological effects such as lithium ions would. The choice of the cation may be different for different pharmaceutically active agents because of the physical properties imparted by the cation to the salt.

Basic pharmaceutically active agents are converted to their salt by partial or complete neutralization (e.g., of amine functionality therein) with an inorganic or organic acid. Appropriate acids include, but are not limited to, hydrochloric acid, sulfuric acid, phosphoric acid, citric acid, maleic acid, gluconic acid, fumaric acid, glycolic acid, and the like.

Amphoteric pharmaceutically active agents maybe converted to a salt by either treatment with a base or an acid such as those listed above. The choice of which method of conversion to a salt for a specific amphoteric pharmaceutically active agent may be dictated by the characteristics of the anionic and cationic salts of that pharmaceutically active agent and further by the choice of the counter-ion from the numerous possibilities already mentioned above.

The granular compositions of the invention can be formed from essentially all relatively water-insoluble pharmaceutically active agents which may be converted to a salt, including combinations of them. Typical of such pharmaceutically active agents are: analgesics, antiinflammatories, antibiotics, antiepileptics, antitussives, expectorants, antihistamines, decongestants, antifungals, cardiovascular drugs, gastrointestinal drugs, and respiratory drugs. Ibuprofen, ketoprofen, diclofenac, naproxen, chlorpromazine, and nifedipine are representative, non-limiting examples of pharmaceutically active agents that derive the benefits of increased dissolution and bioavailability by processing them using the improved methods of this invention.

The drug-containing granulated material of the invention may be compressed into tablets or used to fill capsules.

The following examples are illustrative of the methods of this invention, but are not intended to be limiting. Those skilled in the art will readily understand the benefits of the process described herein, and will appreciate the applications to which it can be applied. All percentages in the following example are by weight unless otherwise clearly indicated.

EXAMPLE 1

In a large, portable tank was placed 39.2 kg of distilled water which was stirred with a Lightnin™ mixer. To this water was added 29.6 kg of hydrolyzed cellulose wetcake, and the mixture was stirred for approximately 10 minutes after addition was complete, forming a smooth slurry containing 17% by weight of hydrolyzed cellulose solids. The pH of this slurry was 3.5. A solution of 30 grams of potassium hydroxide pellets (87%) in 100 grams of distilled water was prepared. Portionwise, this potassium hydroxide was added to the hydrolyzed cellulose slurry, and, after each addition, the pH of the slurry was measured. A total of 46.0 grams of the potassium hydroxide solution was added, raising the pH to 8.6. Next, 400 grams of colloidal silicon dioxide (Cab-O-Sil® M-5) was added to the slurry with continued stirring. After the addition of 600 grams of croscarmellose sodium to the slurry, mixing was continued for approximately 10 minutes. Simultaneously, a solution of 40 grams of sodium lauryl sulfate in 500 grams of distilled water was prepared in a separate container. This solution was then added to the hydrolyzed cellulose slurry with mixing for 10 minutes. To a mixing tank containing 26.0 kg of distilled water was added slowly 3.74 kg of potassium hydroxide pellets (87%). This solution was continuously stirred with a Lightnin™ mixer fitted with a high energy blade. Then 24.0 kg of ibuprofen was added to it. Mixing was continued for at least 15 minutes and until all of the ibuprofen had dissolved. The ibuprofen solution was then pumped into the tank containing the hydrolyzed cellulose slurry. To completely empty the tank that had contained the ibuprofen solution, 2.0 kg of distilled water was used to rinse the tank, and this water was then pumped into the slurry. The slurry was mixed for 10 minutes before the Lightnin™ mixer was replaced by a Greeco rotor stator type mixer. After 10 additional minutes of mixing, the entire slurry was transferred to Groen jacketed mixing tank where it was mixed for 10 minutes at a setting of 3 using both the paddle blade and the impeller mixing blade. The slurry was spray dried using a disk dryer having a diameter of approximately 5 meters at an inlet temperature of 100° C. and an outlet temperature of 48° C. The air flow was approximately 48.14 cubic meters/minute (1700 standard cubic feet/minute), and the feed rate was 1.50 kg/minute. The time required to dry the entire slurry was 135 minutes. The material collected at the dryer discharge weighed 25.2 kg, and an additional 3.5 grams of product was recovered from the cyclone, making a total of 28.7 kilograms of product having a moisture content of 1.92%. The particle size distribution was determined using a stack of sieves in which the top sieve has the largest size openings and each sieve below has smaller size openings than the next higher sieve. The material that was retained on each sieve was weighed. The particle size distribution was determined in this way to be: >50 mesh (>297 microns), 30.8%; 50–60 mesh (297–250 microns), 8.4%; 60–80 mesh (250–177 microns), 19.6%; 80–100 mesh (177–149 microns), 8.6%; 100–120 mesh (149–125 microns), 6.9%; 120–170 mesh (125–88 microns), 11.6%; and <170 mesh (<88 microns), 14.3%. The median particle size thus falls between 177 microns and 250 microns.

A portion (49.25 parts) of this product was dry blended in a twin shell blender with 42.0 parts of Avicel® PH-101 microcrystalline cellulose, 2.5 parts of croscarmellose sodium (Ac-Di-Sol®), 5.0 parts of colloidal silicon dioxide (Cab-O-Sil®), 1.0 part of talc, and 0.25 part of magnesium stearate. This mixture was tableted using a two station Stokes B-2 press fitted with 0.5 inch bevel edge tooling. Each tablet contained 131.95 mg of ibuprofen and had an initial average hardness of 7.2 Kp. These tablets were tested for dissolution of the pharmaceutically active agent under two sets of conditions and were directly compared with commercial Advil® Liqui-gels® comprising solubilized (partial conversion to the potassium salt) ibuprofen (200 mg ibuprofen/capsule, Whitehall Laboratories Inc.). In the first comparative test using a USP apparatus 2 (paddle) at 50 rpm in 900 mL of 0.05 M phosphate buffer at pH 7.2, after 5 minutes 97±1.5% of the ibuprofen in the experimental tablets had dissolved whereas the commercial product had released 1% of the ibuprofen contained therein. The commercial product required 15 minutes to release 65% of the ibuprofen, and one hour to completely release the pharmaceutically active agent. The second test method used the same equipment, but substituted a 0.1 N hydrochloric acid solution for the phosphate buffer. Under these conditions 29±0.6% of the ibuprofen was released from the tablets of this invention after five minutes whereas the commercial liqui-gels released 1% of the pharmaceutically active agent. After one hour these values were 39±1.2% and 11%, respectively. At the conclusion of the hour, the pH of the solution was adjusted to greater than 6.0 by the addition of 5.3M sodium hydroxide. The dissolution measured five minutes after the pH adjustment showed that 84±10.1% of the ibuprofen had dissolved from the experimental tablets, but 15±4.2% of it had dissolved from the Liqui-gels. Two additional sets of ibuprofen-containing tablets (each containing 200 mg of the pharmaceutically active agent) were prepared using the method described above. One set of tablets used the spray-dried formulation of Example 1, and the other set of tablets was prepared using the free ibuprofen acid as formulated by the method of U.S. Pat. No. 5,858,409. Both were tested in 0.5M phosphate buffer at pH 7.2 and at pH 5.8. After 5 minutes at pH 7.2, 95–97% of the ibuprofen had dissolved, indicating little difference in the rate of dissolution of both tablets; however, after 5 minutes at pH 5.8, which is more representative of early intestinal pH, the tablets of this invention had released 82% of the pharmaceutically active agent whereas 39% of the free acid was released. After 30 minutes, 97% of the pharmaceutically active agent in the tablets of this invention had dissolved as compared with 85% of the free acid from the tablets of the prior art formulation.

EXAMPLE 2

A dried, 50/50 mixture of potassium ibuprofen and ibuprofen was prepared for granulating with excipients for subsequent tablet formation. 666.60 g of ibuprofen (BASF) was combined with 100.42 g potassium hydroxide pellets (Baker) and 490.47 g DI water. As the potassium hydroxide pellets contain about 10% water, there is actually about 90.89 g potassium hydroxide and 500 g DI water. A Lightnin™ mixer was used to mix the water and potassium hydroxide pellets until the potassium hydroxide dissolved. The ibuprofen was slowly added until all of the ibuprofen went into solution. The solution was then dried in a vacuum oven (VWR table top model) for 8 days at 25 psi at a temperature of about 50° C. The dried potassium ibuprofen was screened by hand through a 30 mesh sieve.

Cab-O-Sil® fumed silica was screened by hand through a 30 mesh sieve. The following ingredients were then dry mixed for 10 minutes in the smallest PK: potassium ibuprofen (50/50 potassium ibuprofen/ibuprofen, dried)(32.29 g), Avicel® microcrystalline cellulose PH-103 (55.42 g), Ac-Di-Sol® croscarmellose (3.85 g), screened Cab-O-Sil® fumed silica (5.37 g), and sodium laurel sulfate (SLS)(0.07 g). Talc (1.0 g) was hand screened through a 30 mesh sieve, charged into the PK mixer, and the ingredients were mixed for an additional 5 minutes. Sterotex (hydrogenated vegetable oil) (2.0 g) was hand screened with a 30 mesh sieve and charged into the mixer. The formulation was then mixed for another 5 minutes. The formulation was then discharged into a polybag.

The mixture was tableted using a Stokes 512 press fitted with ½ standard concave round tooling using two stations. Each tablet had a weight of 676.6 mg and a hardness between 4–12 kp.

The tablets capped at all hardness levels tested (4–12 kp) with severe edge wear evident. The tablets caused filming of the punches, and sticking of the formulation to the center of the upper punches was evident after compression of about 100 g of the formulation. Disintegration was in the 45 second range at 4 kp and in the 1.5 minute range at 12 kp.

EXAMPLE 3

A granular preparation of ibuprofen (which had been converted at least partially into potassium ibuprofen) was spray-dried with hydrolyzed cellulose and was designated PI. Separately, free acid ibuprofen was spray-dried with hydrolyzed cellulose and designated FAI. In order to neutralize the hydrolyzed cellulose, some ammonia was added to the FAI mixture before drying. The addition of ammonia does not appreciably cause formation of ibuprofen salt. The dissolution profiles of the two formulations were examined in 900 ml phosphate buffer (pH=4.5) at 50 rpm using the paddle method as described in Example 1.

Figure 2:
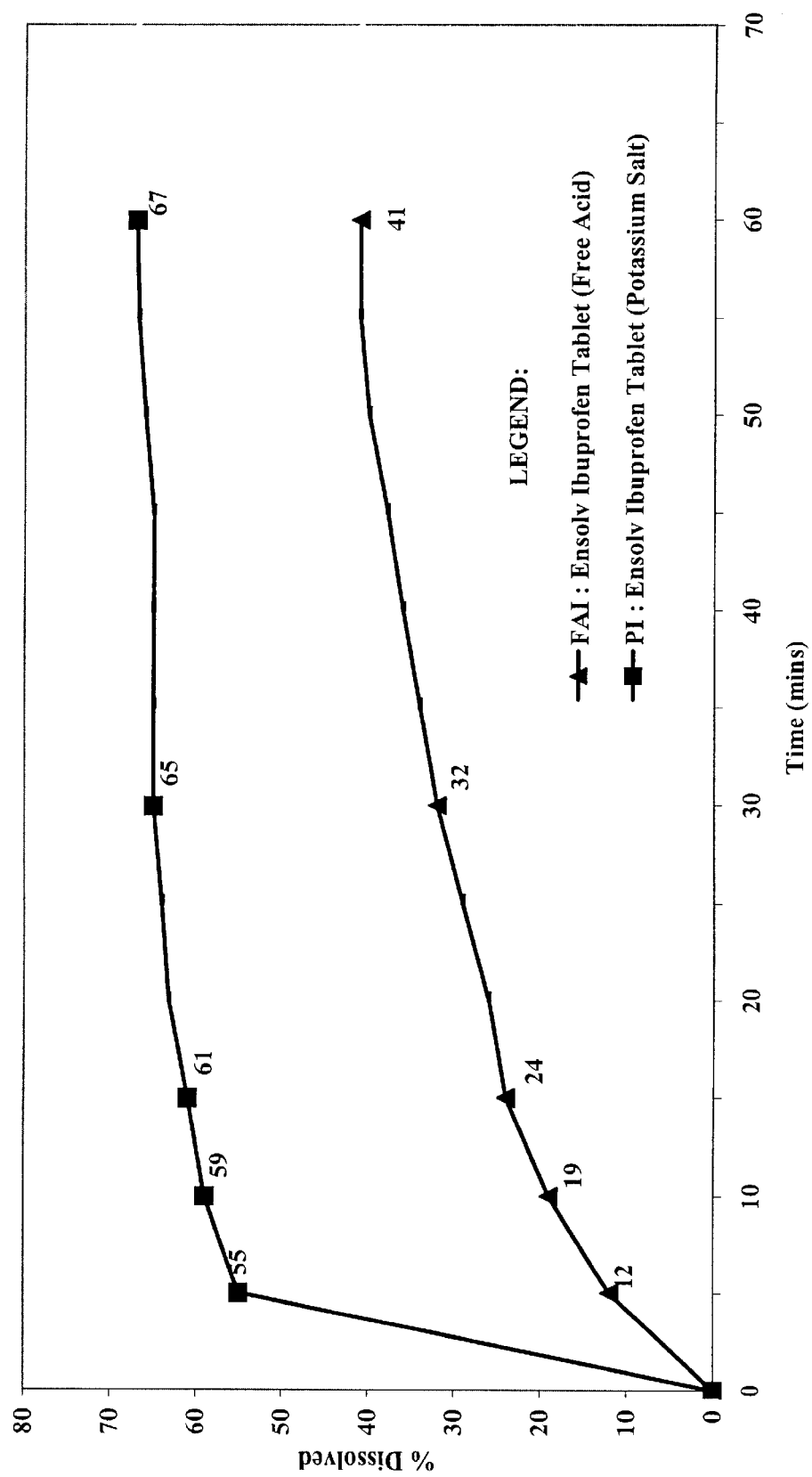
FIG. 2 shows dissolution profiles of free acid ibuprofen spray dried with hydrolyzed cellulose (FAI), and ibuprofen which had been at least partially converted into potassium salt and spray dried with hydrolyzed cellulose (PI).

As shown in FIG. 2, at 5 minutes, 55% of the potassium ibuprofen had dissolved compared with 12% of the ibuprofen free acid. At 30 minutes, 65% of the potassium ibuprofen had dissolved as compared with 32% of the ibuprofen free acid. At 60 minutes, 67% of the potassium ibuprofen had dissolved compared with 41% of the ibuprofen free acid.

EXAMPLE 4

A granular preparation of ibuprofen (which had been converted at least partially into potassium ibuprofen) was spray-dried with hydrolyzed cellulose, was formed into tablets, film-coated, and designated PI. Separately, free acid ibuprofen was spray-dried with hydrolyzed cellulose, formed into tablets, film-coated and designated FAI. As in Example 3, FAI was prepared with the addition of a small amount of ammonia to neutralize the hydrolyzed cellulose mixture. The tablets were subjected to dissolution profile analysis in 900 ml of 0.1N HCl at 50 rpm using the paddle method as described in Example 1.

As shown in FIG. 3, at 5 minutes at low pH (below the pKa of ibuprofen) 25% of the potassium ibuprofen had dissolved compared with 5% of the ibuprofen free acid. At 30 minutes, 31% of the potassium ibuprofen had dissolved compared with 18% of the ibuprofen free acid. At 60 minutes, the pH of the solution was adjusted to greater than 6.0 with 5.3M NaOH. At the higher pH, the remainder of each tablet rapidly dissolved. The increased solubility of potassium ibuprofen at low pH may have the advantage of rapid uptake of drug into the circulation while still in the acidic environment of the stomach as compared to ibuprofen free acid and conventional ibuprofen preparations.

As shown in FIG. 1, there is no appreciable dissolution of ibuprofen in the unprocessed, free acid form or the free acid form processed with the hydrolyzed cellulose when the pH is below about 6.0. At a pH of about 6.0, the solubility of the free acid formulated with the hydrolyzed cellulose was 0.134 mg/ml as compared to the solubility of the spray dried potassium ibuprofen, which was 2.42 mg/ml (18 fold greater solubility). Even more striking is the fact that at low pH (less than about 2) the solubility of the potassium ibuprofen is slightly greater than the solubility of the unprocessed ibuprofen or the ibuprofen free acid spray-dried with hydrolyzed cellulose at a pH of about 6.0.

We claim:

1. A dry granular composition comprising hydrolyzed cellulose in immixture with at least one relatively water-insoluble pharmaceutically active agent in its more water-soluble form wherein said pharmaceutically active agent in its more water-soluble salt form comprises about 30% to about 80% of said composition and comprises a mixture of ibuprofen and its potassium salt in a ratio of about 3:1 to 1:1; said hydrolyzed cellulose comprises about 20% to about 70% of said composition; said composition additionally comprising about 1% to about 10% of croscarmellose sodium, about 0.5% to about 5% of colloidial silicon dioxide, and about 0.05% to about 0.4% sodium lauryl sulfate; all percentages being by weight of the dry granules.

* * * * *